US012697482B2

(12) United States Patent
Anstadt

(10) Patent No.: US 12,697,482 B2
(45) Date of Patent: Aug. 4, 2026

(54) SYSTEM AND METHOD FOR PROVIDING IMPROVED CARDIAC PUMP FUNCTION THROUGH SYNCHRONIZATION WITH THE NATURAL MECHANICAL CONTRACTIONS OF THE HEART

(71) Applicant: Lifebridge Technologies, LLC, Dayton, OH (US)

(72) Inventor: Mark P. Anstadt, Kettering, OH (US)

(73) Assignee: Lifebridge Technologies LLC, Dayton, OH (US)

( * ) Notice: Subject to any disclaimer, the term of this patent is extended or adjusted under 35 U.S.C. 154(b) by 1009 days.

(21) Appl. No.: 17/825,343

(22) Filed: May 26, 2022

(65) Prior Publication Data

US 2022/0280771 A1 Sep. 8, 2022

Related U.S. Application Data

(63) Continuation-in-part of application No. 17/208,776, filed on Mar. 22, 2021, now Pat. No. 11,383,076.
(Continued)

(51) Int. Cl.
 *A61M 60/569* (2021.01)
 *A61M 60/191* (2021.01)
 (Continued)

(52) U.S. Cl.
 CPC ........ *A61M 60/569* (2021.01); *A61M 60/191* (2021.01); *A61M 60/289* (2021.01); *A61M 60/468* (2021.01); *A61M 60/515* (2021.01)

(58) Field of Classification Search
 CPC .............. A61M 60/191; A61M 60/289; A61M 60/468; A61M 60/515; A61M 60/569; A61M 2230/04; A61M 2205/33
 See application file for complete search history.

(56) References Cited

U.S. PATENT DOCUMENTS

| 2,826,193 A | 3/1958 | Vineberg |
| 2,889,780 A | 6/1959 | Binford |

(Continued)

FOREIGN PATENT DOCUMENTS

| JP | 2002-532189 | 10/2002 |
| JP | 2007-524464 | 10/2007 |

(Continued)

OTHER PUBLICATIONS

Song, Ruoyu et al. (2019). Causes of Desktop FDM Fabrication Failures in an Open Studio Environment. Procedia CIRP. 80. 494-499. (Year: 2019).

(Continued)

*Primary Examiner* — Pamela M. Bays
(74) *Attorney, Agent, or Firm* — LaMorte & Associates, P.C.

(57) ABSTRACT

A control system for a cardiac support device and the method of supporting the functionality and synchronized contraction of a heart. An optimal strain profile is calculated for a healthy heart. The cardiac support device is attached to the heart and a true ventricular strain profile is measured. The cardiac support device applies external forces to the heart, therein altering said ventricular strain profile of said heart to be closer to the optimal strain profile. The cardiac support device is dynamically controlled to synchronize with the beating rhythm of the heart. The external forces have an applied strain profile. The applied strain profile has a peak strain, a time to peak strain, and a cycle time. These variables can be adjusted either individually or in combinations to fine tune the cardiac support device and cause the altered strain profile of the heart to be closer to the optimal strain profile.

15 Claims, 8 Drawing Sheets

Related U.S. Application Data

(60) Provisional application No. 63/086,478, filed on Oct. 1, 2020.

(51) Int. Cl.
    *A61M 60/289*     (2021.01)
    *A61M 60/468*     (2021.01)
    *A61M 60/515*     (2021.01)

(56)         References Cited

U.S. PATENT DOCUMENTS

| | | |
|---|---|---|
| 3,053,249 A | 9/1962 | Smith |
| 3,233,607 A | 2/1966 | Bolle |
| 3,279,464 A | 10/1966 | Kline |
| 3,304,501 A | 2/1967 | Ruthenberg |
| 3,371,662 A | 3/1968 | Heid |
| 3,376,863 A | 4/1968 | Kolobow |
| 3,449,767 A | 6/1969 | Bolie |
| 3,455,298 A | 7/1969 | Anstadt |
| 3,478,737 A | 11/1969 | Rassman |
| 3,513,836 A | 5/1970 | Sausse |
| 3,587,567 A | 6/1971 | Schiff |
| 3,590,815 A | 7/1971 | Schiff |
| 3,613,672 A | 10/1971 | Schiff |
| 3,674,381 A | 7/1972 | Schiff |
| 4,048,990 A | 9/1977 | Goetz |
| 4,192,293 A | 3/1980 | Asrican |
| 4,281,669 A | 8/1981 | MacGregor |
| 4,448,190 A | 5/1984 | Freeman |
| 4,536,893 A | 8/1985 | Parravicini |
| 4,609,176 A | 9/1986 | Powers |
| 4,621,617 A | 11/1986 | Sharma |
| 4,662,358 A | 5/1987 | Farrar |
| 4,684,143 A | 8/1987 | Sata |
| 4,957,477 A | 9/1990 | Lundback |
| 4,979,936 A | 12/1990 | Stephenson |
| 5,066,111 A | 11/1991 | Inokuchi |
| 5,089,017 A | 2/1992 | Young |
| 5,098,369 A | 3/1992 | Heilman et al. |
| 5,098,442 A | 3/1992 | Grandjean |
| 5,119,804 A | 6/1992 | Anstadt |
| 5,131,905 A | 7/1992 | Grooters |
| 5,156,154 A | 10/1992 | Valenta, Jr. et al. |
| 5,158,978 A | 10/1992 | Rubin |
| 5,169,381 A | 12/1992 | Snyders |
| 5,199,804 A | 4/1993 | Rimbey et al. |
| 5,205,722 A | 4/1993 | Hammond |
| 5,256,132 A | 10/1993 | Snyders |
| 5,273,518 A | 12/1993 | Lee et al. |
| 5,322,067 A | 6/1994 | Prater |
| 5,330,505 A | 7/1994 | Cohen |
| 5,364,337 A | 11/1994 | Guiraudon et al. |
| 5,368,451 A | 11/1994 | Hammond |
| 5,374,287 A | 12/1994 | Rubin |
| 5,383,840 A | 1/1995 | Heilman et al. |
| 5,385,528 A | 1/1995 | Wilk |
| 5,429,584 A | 7/1995 | Chu |
| 5,476,502 A | 12/1995 | Rubin |
| 5,496,353 A | 3/1996 | Grandjean et al. |
| 5,533,958 A | 7/1996 | Wilk |
| 5,558,617 A | 9/1996 | Heilman et al. |
| 5,562,595 A | 10/1996 | Neisz |
| 5,658,237 A | 8/1997 | Francischelli |
| 5,674,259 A | 10/1997 | Gray |
| 5,697,884 A | 12/1997 | Francischelli et al. |
| 5,697,952 A | 12/1997 | Francischelli et al. |
| 5,707,336 A | 1/1998 | Rubin |
| 5,713,954 A | 2/1998 | Rosenberg et al. |
| 5,716,379 A | 2/1998 | Bourgeios et al. |
| 5,738,627 A | 4/1998 | Kovacs et al. |
| 5,749,839 A | 5/1998 | Kovacs |
| 5,769,800 A | 6/1998 | Gelfand et al. |
| 5,800,334 A | 9/1998 | Wilk |
| 5,861,558 A | 1/1999 | Buhl et al. |
| 5,876,345 A | 3/1999 | Eaton et al. |
| 5,902,229 A | 5/1999 | Tsitlik et al. |
| 5,908,378 A | 6/1999 | Kovacs et al. |
| 5,910,124 A | 6/1999 | Rubin |
| 5,919,209 A | 7/1999 | Schouten |
| 5,971,910 A | 10/1999 | Tsitlik et al. |
| 5,971,911 A | 10/1999 | Wilk |
| 5,980,571 A | 11/1999 | Nomura et al. |
| 6,042,532 A | 3/2000 | Freed et al. |
| 6,044,298 A | 3/2000 | Salo et al. |
| 6,059,750 A | 5/2000 | Fogarty et al. |
| 6,076,013 A | 6/2000 | Brennan et al. |
| 6,095,968 A | 8/2000 | Snyders |
| 6,110,098 A | 8/2000 | Renirie et al. |
| 6,123,726 A | 9/2000 | Mori et al. |
| 6,132,363 A | 10/2000 | Freed et al. |
| 6,183,412 B1 | 2/2001 | Benkowski et al. |
| 6,206,820 B1 | 3/2001 | Kazi et al. |
| 6,224,540 B1 | 5/2001 | Lederman et al. |
| 6,238,334 B1 | 5/2001 | Easterbrook, III et al. |
| 6,251,061 B1 | 6/2001 | Hastings et al. |
| 6,254,525 B1 | 7/2001 | Reinhardt et al. |
| 6,282,445 B1 | 8/2001 | Reinhardt et al. |
| 6,298,266 B1 | 10/2001 | Rubin et al. |
| 6,309,380 B1 | 10/2001 | Larson et al. |
| 6,328,689 B1 | 12/2001 | Gonzalez et al. |
| 6,408,205 B1 | 6/2002 | Renirie et al. |
| 6,432,039 B1 | 8/2002 | Wardle |
| 6,438,411 B1 | 8/2002 | Guttman et al. |
| 6,464,655 B1 | 10/2002 | Shahinpoor |
| 6,485,407 B2 | 11/2002 | Alferness et al. |
| 6,508,756 B1 | 1/2003 | Kung et al. |
| 6,540,659 B1 | 4/2003 | Milbocker |
| 6,547,716 B1 | 4/2003 | Milbocker |
| 6,572,534 B1 | 6/2003 | Milbocker et al. |
| 6,602,182 B1 | 8/2003 | Milbocker |
| 6,612,978 B2 | 9/2003 | Lau et al. |
| 6,616,596 B1 | 9/2003 | Milbocker |
| 6,622,045 B2 | 9/2003 | Snell et al. |
| 6,626,821 B1 | 9/2003 | Kung et al. |
| 6,641,604 B1 | 11/2003 | Adelman et al. |
| 6,682,474 B2 | 1/2004 | Lau et al. |
| 6,730,016 B1 | 5/2004 | Cox et al. |
| 6,757,561 B2 | 6/2004 | Rubin et al. |
| 6,808,483 B1 | 10/2004 | Ortiz et al. |
| 6,846,296 B1 | 1/2005 | Milbocker et al. |
| 6,971,127 B2 | 12/2005 | Richards |
| 7,331,221 B2 | 2/2008 | Wise et al. |
| 7,494,459 B2 | 2/2009 | Anstadt et al. |
| 7,871,366 B2 | 1/2011 | Criscione et al. |
| 8,187,160 B2 | 5/2012 | Criscione et al. |
| 8,460,181 B2 | 6/2013 | Saadat et al. |
| 10,058,647 B2 | 8/2018 | Roche et al. |
| 10,463,496 B2 | 11/2019 | Criscione et al. |
| 11,191,944 B2 | 12/2021 | Tuval et al. |
| 11,511,102 B2 | 11/2022 | Criscione et al. |
| 11,752,321 B2 | 9/2023 | Pilla et al. |
| 12,115,363 B1 | 10/2024 | Anstadt |
| 12,161,857 B2 | 12/2024 | Saul et al. |
| 12,226,622 B2 | 2/2025 | Kheradvar et al. |
| 2001/0002445 A1 | 5/2001 | Vesely |
| 2001/0041821 A1 | 11/2001 | Wilk |
| 2002/0173693 A1* | 11/2002 | Landesberg ........ A61M 60/441 600/16 |
| 2003/0032855 A1 | 2/2003 | Shahinpoor |
| 2004/0010180 A1 | 1/2004 | Scorvo |
| 2004/0024315 A1 | 2/2004 | Chalana |
| 2004/0059183 A1 | 3/2004 | Jozef et al. |
| 2004/0078067 A1 | 4/2004 | Thompson et al. |
| 2004/0102674 A1 | 5/2004 | Zadini et al. |
| 2004/0116769 A1 | 6/2004 | Jassawalla |
| 2004/0167375 A1 | 8/2004 | Couvillon |
| 2004/0225177 A1 | 11/2004 | Coleman et al. |
| 2004/0267086 A1 | 12/2004 | Anstadt et al. |
| 2005/0004420 A1* | 1/2005 | Criscione ............. A61F 2/2481 600/16 |
| 2005/0113632 A1 | 5/2005 | Ortiz et al. |
| 2005/0148814 A1 | 7/2005 | Fischi et al. |
| 2005/0234289 A1 | 10/2005 | Anstadt et al. |
| 2006/0106442 A1 | 5/2006 | Richardson et al. |

(56) References Cited

U.S. PATENT DOCUMENTS

| | | | |
|---|---|---|---|
| 2006/0129025 A1 | 6/2006 | Levine et al. | |
| 2006/0142634 A1 | 6/2006 | Anstadt et al. | |
| 2006/0167334 A1* | 7/2006 | Anstadt | A61M 60/191 |
| | | | 600/17 |
| 2006/0211909 A1 | 9/2006 | Anstadt et al. | |
| 2007/0197859 A1 | 8/2007 | Schaer et al. | |
| 2008/0081944 A1 | 4/2008 | Lau et al. | |
| 2008/0194905 A1* | 8/2008 | Walsh | A61M 60/468 |
| | | | 600/17 |
| 2008/0255629 A1 | 10/2008 | Jenson | |
| 2008/0257412 A1 | 10/2008 | Gordon | |
| 2009/0036730 A1 | 2/2009 | Criscione | |
| 2009/0099498 A1 | 4/2009 | Demers et al. | |
| 2010/0081867 A1 | 4/2010 | Fishler | |
| 2010/0152523 A1 | 6/2010 | MacDonald et al. | |
| 2010/0191071 A1 | 7/2010 | Anderson | |
| 2011/0196189 A1 | 8/2011 | Milbocker | |
| 2011/0288367 A1 | 11/2011 | Miller | |
| 2012/0095498 A1 | 4/2012 | Stefanchik et al. | |
| 2013/0102849 A1 | 4/2013 | Criscione | |
| 2015/0018607 A1 | 1/2015 | Akita | |
| 2015/0080640 A1 | 3/2015 | Lillehei | |
| 2016/0101230 A1 | 4/2016 | Ochsner | |
| 2016/0151552 A1 | 6/2016 | Solem | |
| 2016/0262889 A1 | 9/2016 | Laham et al. | |
| 2016/0346449 A1 | 12/2016 | Roche | |
| 2017/0071675 A1* | 3/2017 | Dawoud | A61N 1/0587 |
| 2017/0258593 A1 | 9/2017 | Good et al. | |
| 2018/0153709 A1 | 6/2018 | Hunter | |
| 2019/0209759 A1 | 7/2019 | Vasilyev et al. | |
| 2019/0224395 A1 | 7/2019 | Pilla et al. | |
| 2020/0085579 A1 | 3/2020 | Kim | |
| 2022/0013211 A1 | 1/2022 | Steinberg | |
| 2022/0249830 A1 | 8/2022 | Kanz | |
| 2023/0060284 A1 | 3/2023 | Siess et al. | |
| 2023/0071248 A1 | 3/2023 | Keenan et al. | |
| 2024/0082566 A1 | 3/2024 | Anstadt | |
| 2024/0216652 A1 | 7/2024 | Keenan et al. | |
| 2024/0269459 A1 | 8/2024 | Schellenberg et al. | |

FOREIGN PATENT DOCUMENTS

| | | |
|---|---|---|
| WO | WO 00/78375 | 12/2000 |
| WO | WO2005/091860 | 10/2005 |
| WO | WO2006/122036 | 11/2006 |
| WO | WO2008/127607 | 10/2008 |

OTHER PUBLICATIONS

Devore. "24-segment sphericity index: a new technique to evaluate fetal cardiac diastolic shape" 650-658. Ultrasound in obstetrics & gynecology. Https://pubmed.ncbi.nlm.nih.gov/28437575/. May 2018; <DOI: 10.1002/uog. 17505>.

* cited by examiner

SYSTEM AND METHOD FOR PROVIDING IMPROVED CARDIAC PUMP FUNCTION THROUGH SYNCHRONIZATION WITH THE NATURAL MECHANICAL CONTRACTIONS OF THE HEART

RELATED APPLICATIONS

This application is a continuation-in-part of U.S. U.S. Pat. No. 11,383,076, filed Mar. 22, 2021, which claims the priority of U.S. Provisional Patent Application No. 63/086,478, filed Oct. 1, 2020, the entirety of which are herein incorporated by reference.

BACKGROUND OF THE INVENTION

1. Field of the Invention

In general, the present invention relates to auxiliary cardiac support devices that directly contact the heart and assist the heart in pumping blood. More particularly, the present invention relates to control systems that activate the auxiliary cardiac support devices and attempt to control the operation of the auxiliary cardiac support devices in a manner that assists the functionality of the heart.

2. Prior Art Description

There are medical circumstances when it is beneficial to attach a cardiac support device to, or near, the exterior of an injured or failing heart. The cardiac support device supplements the pumping action of the heart by imparting forces directly onto the exterior of the heart in an effort to artificially maintain the physiologic function of the heart. Most of these cardiac support devices mechanically compress the heart to aid systolic pump function and/or mechanically expand the heart to aid in diastolic pump function.

The heart is a complex organ. When the heart pumps, various muscle tissue within the heart contracts in a very specific pattern. During each heartbeat, a healthy heart has an orderly progression of depolarization that starts with pacemaker cells in the sinoatrial node. The progression spreads throughout the atrium and passes through the atrioventricular node into the bundle of His and into the Purkinje fibers. Lastly, the progression spreads throughout the ventricles. The electrical impulses created by the progression can be detected using electrocardiogram equipment. The electrical impulses created by the progression create a corresponding pattern of contractions within the heart. When the ventricles of the heart contract, the contracting cells have a unique pattern of contraction. This pattern of contraction is termed mechanical cardiac synchrony. The mechanical cardiac synchrony produces a coordinated mechanical expulsion of blood from the ventricles. There also is a mechanical synchrony for the progression of diastolic contractions during the filling of the ventricles. A normal, healthy heart exhibits normal mechanical cardiac synchrony. A diseased, damaged, or failing heart often does not have normal mechanical cardiac synchrony and is referred to as being dyssynchronous.

There are three main electrical components contained within a heartbeat waveform that are recorded in an electrocardiogram. These three components create corresponding mechanical contractions is the tissues of the heart. The three main electrical components include the P-wave, the QRS complex, and the T-wave. The P-wave represents depolarization of the atria, wherein atrial depolarization spreads from the SA node towards the AV node, and from the right atrium to the left atrium. This process typically takes about 80 milliseconds. The QRS complex, which represents depolarization of the ventricles, typically takes between 80 milliseconds and 100 milliseconds. The ventricles have more muscle mass than the atria. Accordingly, the QRS complex usually has a larger amplitude than does the P-wave. Since the QRS complex corresponds to ventricular contraction and is a prominent signal, the QRS complex is often used to determine the "time" of contraction as the heart beats. Finally, the T-wave represents the repolarization of the ventricles. This process typically takes about 160 milliseconds. Accordingly, it will be understood that a heartbeat is a progression of complex contractions of the heart. It is this complex progression of contractions that is often adversely affected when the heart becomes diseased or damaged. A damaged or diseased heart contracts with "dysynchrony" and pumps blood in an inefficient manner.

There are many cardiac support devices in the prior art that can apply forces to the exterior of the heart. Some devices, such as U.S. Pat. No. 7,494,459, to Anstadt and U.S. Pat. No. 6,076,013 to Brennan, disclose cup shaped devices that encircle most of the ventricles. Other devices, such as U.S. Patent Application Publication No. 2015/0080640 to Lillehei and U.S. Patent Application Publication No. 2007/0197859 to Schaer et al., disclose bands that surround only a portion of the ventricles. One of the problems associated with such prior art cardiac support devices is that the devices are mechanisms that expand and/or contract when instructed. Accordingly, the operation of such devices tend to be binary, that is on/off. It is therefore very difficult to control a cardiac support device so that the cardiac support device accurately assists a heart in achieving the complex mechanical synchrony of a healthy heart. Most often, the result is a compromise where hemodynamic feedback is used to control the cardiac support device. Such control of the cardiac support device can be used to mimic some of the complex contractions of the heart, but not all. The result is that cardiac support device may fight the natural contractions of the heart in certain places at certain times. This can further fatigue some heart tissue and make the heart pump less effectively. Furthermore, by being out of synchronization with the heart, the cardiac support device can hinder the heart in recovering a normal stable rhythm.

A need therefore exists for an improved control system for controlling a cardiac support device. In this manner, the cardiac support device can apply appropriated forces to the heart in a manner that assist a diseased or damages heart to both achieve better pacing synchrony and to achieve better mechanical cardiac synchrony. This need is met by the present invention as described and claimed below.

SUMMARY OF THE INVENTION

The present invention is a control system for a cardiac support device and the method of supporting the functionality of a heart with the cardiac support device. In accordance with the methodology, an optimal strain profile is calculated for a healthy heart of an average person having the same physiological heart characteristics as does the patient.

A ventricular strain profile is measured for the actual heart, using strain gauges or strain scans. The cardiac support device is placed in position where it can apply external forces to the heart. The cardiac support device applies external forces to the heart, therein altering the ventricular strain profile of the heart to be closer to the optimal strain profile. The cardiac support device is dynamically controlled to approach, and hopefully achieve, proper rhythm and proper mechanical cardiac synchrony.

The external forces applied to the heart by the cardiac support device cause the heart to have a modified strain profile. The modified strain profile has a peak strain, a time to peak strain, and a cycle time. These variables can be adjusted either individually, or in combinations, to fine tune the cardiac support device and cause the modified strain profile of the heart to be closer to the optimal strain profile.

The optimal strain profile is calculated using the physiology of the patient's heart. As the cardiac support device applies external forces to the heart, the size of the heart changes and the beat rhythm changes. The changes in size and/or the beat rhythm can be used to update the optimal strain profile in a feedback loop.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention system and methodology can be embodied in many ways, only two exemplary embodiments are illustrated. The exemplary embodiments are being shown for the purposes of explanation and description. The exemplary embodiments are selected in order to set forth some of the best modes contemplated for the invention. The illustrated embodiments, however, are merely exemplary and should not be considered as limitations when interpreting the scope of the appended claims.

Figure 1:
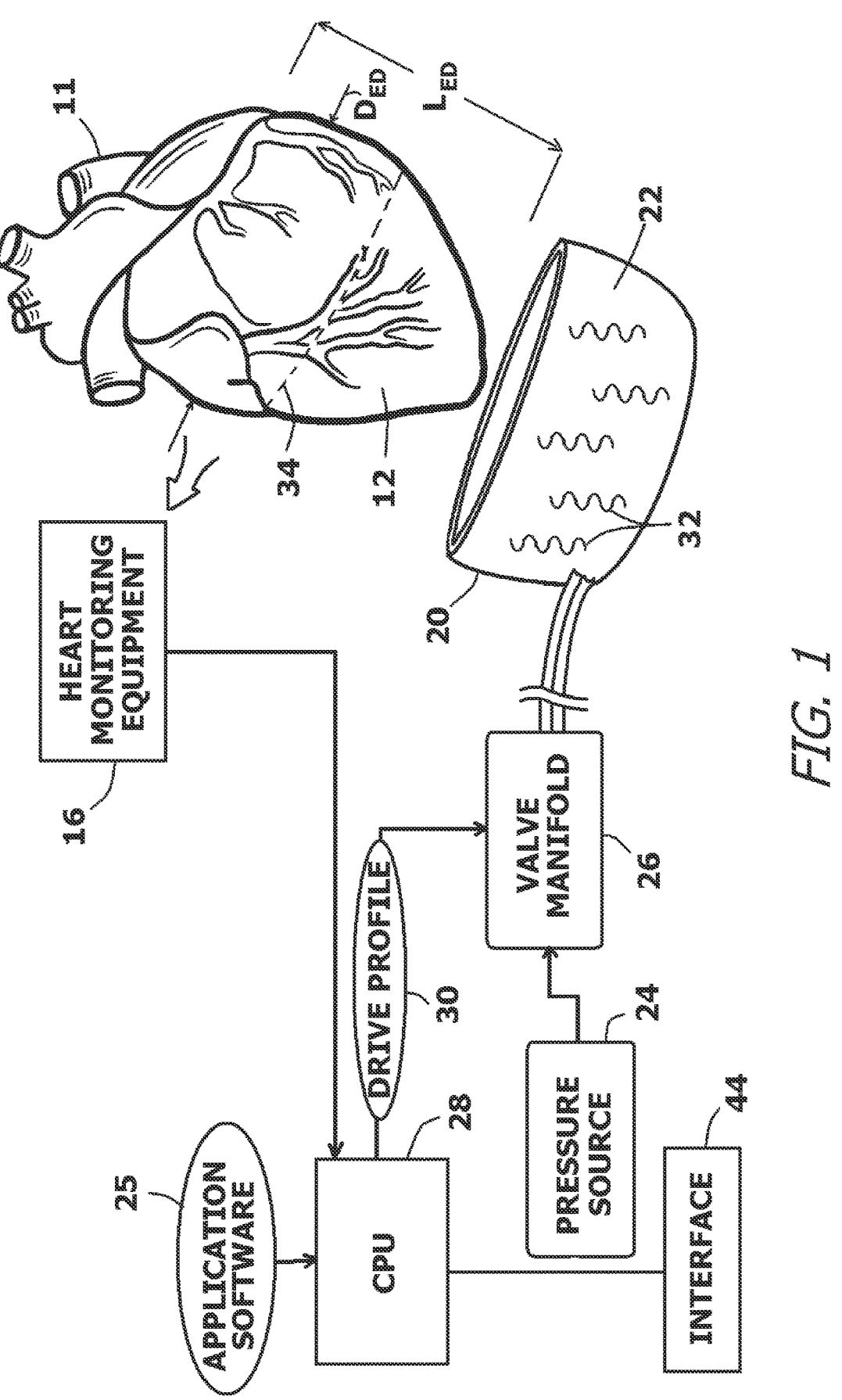
FIG. 1 is an exemplary schematic overview of the present invention system shown in conjunction with a heart.

Referring to FIG. 1, an exemplary embodiment illustrating the present invention system 10 is shown. In the illustrated embodiment, a heart 11 is shown for better understanding of context. Every individual has a heart of a different size. The heart 11 has measurable dimensions that are unique for a particular person. One of the measurable dimensions is diameter D (ED). The diameter D (ED) corresponds to the diameter of the myocardium as measured at the end of the diastolic cycle. Likewise, the heart 11 has a measurable length L (ED) that corresponds to the length of the ventricles at the end of the diastolic cycle. These dimensions of the heart 11 can be readily obtained from various medical scanning equipment, such as x-rays, ultrasounds, MRIs, and the like. Furthermore, it is understood that the heart 11 has a heartbeat, wherein the heart 11 contracts with a regular rhythm. Although the rhythm can be irregular, it has a general average rate of contraction over increments of time. The rhythm of the heart 11 can also be quantified using heart monitoring equipment 16, such as a blood pressure monitor or an ECG unit.

The measured diameter $D_{(ED)}$ and measured length $L_{(ED)}$ of the heart 11 can be used to accurately calculate other characteristics of the heart 11. For instance, the measured diameter $D_{(ED)}$ correlates directly to the volume $V_{(ED)}$ within the ventricles 12 at the end of the diastolic cycle. The relationship between the measured diameter $D_{(ED)}$ and the measured volume $V_{(ED)}$ is explained in detail in U.S. Pat. No. 11,383,076, the disclosure of which is herein incorporated by reference.

A cardiac support device 20 is provided. There are multiple cardiac support devices 20 in the prior art and in the commercial marketplace, many of which can be adapted for use with the present invention system 10. The cardiac support device 20 illustrated is indicative of those known and available. Some cardiac support devices are positioned adjacent to the heart and externally apply mechanical forces to heart in the area of contact. In the illustrated embodiment, the cardiac support device 20 contains a cup or band 22 that surrounds the ventricles 12 of the heart 11 in part or in whole. Depending upon the make and model of the cardiac support device 20 selected, the band 22 expands and/or contracts, therein mechanically assisting the pumping action of the heart 10. The cardiac support device 20 contains various internal tubes and compartments that expand or contract depending upon the pressure supplied to those tubes and compartments. The pressure can be pneumatically or hydraulically supplied from an external pressure source 24, such as a hydraulic pump or air compressor. The pressure supplied to the various tubes and compartment is controlled by a valve manifold 26. The operation of the valve manifold 26 is controlled by application software 25 running in a central processing unit 28. The application software 25 produces drive profiles 30 that control the valve manifold 26. The drive profiles 30 cause the valve manifold 26 to regulate the pressures in the cardiac support device 20, wherein the cardiac support device 20 applies forces to the heart 11 that reflect the drive profiles 30. The present invention system 10 creates feedback between the heart 11 and the central processing unit 28, so that the drive profiles 30 controlling the operations of the cardiac support device 20 can better synchronize with the natural contractions of the heart 11.

Figure 2:
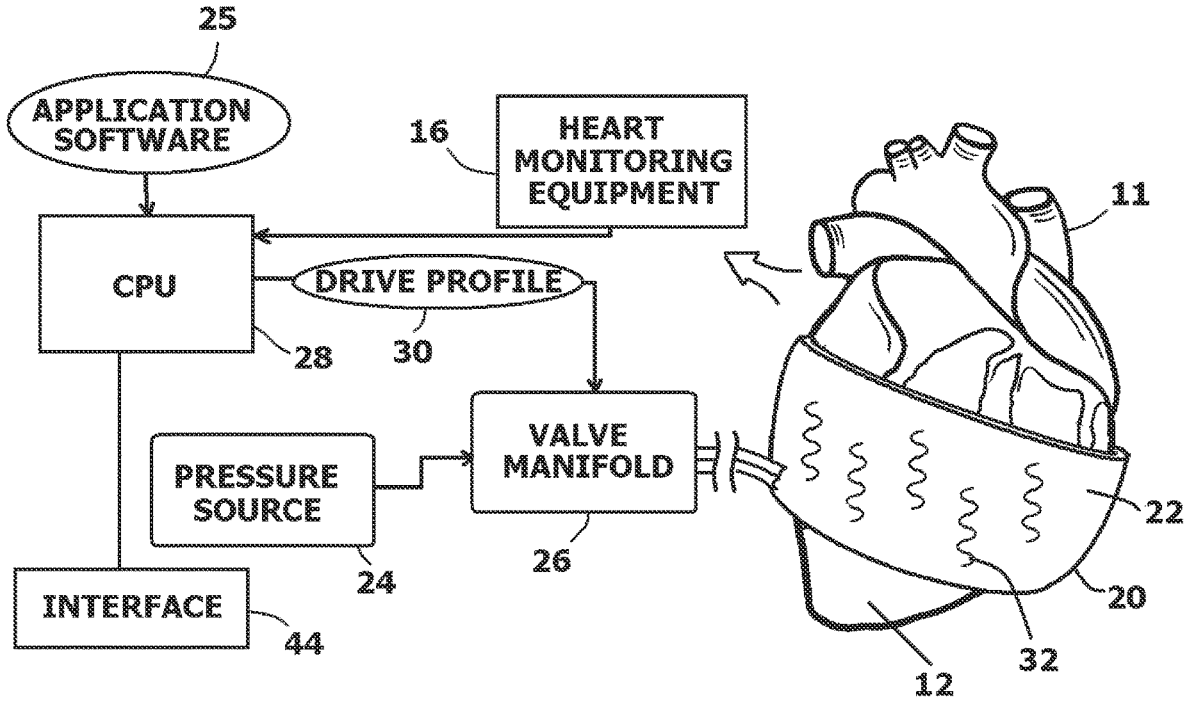
FIG. 2 shows the exemplary embodiment of FIG. 1 engaging the heart.

The pumping characteristics of the heart 11 can be expressed using strain rate profiles. The strain rate profiles can be used to extrapolate the drive profiles 30 that are utilized by the central processing unit 28 to operate the cardiac support device 20. As can be seen in FIG. 2, the cardiac support device 20 is placed around the ventricles 12 of the heart 11. The ventricular strain profile of the heart is directly measured. This can be accomplished passively, using data from X-ray scan, MRI scans or other strain scans that image the heart. Alternatively, the ventricular strain profile can be actively obtained by placing strain gauges 32 on the heart 11. The active process of measure strain using strain gauges 32 is illustrated. Strain gauges 32, or the alternative strain scan, are used to directly measure any strain ε(t) experienced at the cardiac support device 20. If strain gauges 32 are used, the strain gauges 32 can be retroactively added to the device with adhesive. However, it is preferred that a cardiac support device 32 manufactured with integral strain gauges 32 be used.

When the effects of the cardiac support device 20 are ignored, the strain ε(t) is created by the inherent function of the heart 11. This assumes the heart 11 is not completely arrested and is capable of providing some pumping function. Should the heart 11 be fully arrested, the strain ε(t) would solely represent the function imparted by the cardiac support device 20. The goal of the overall system 10 is to regulate the cardiac support device 20 so that the forces applied by the cardiac support device 20, combined with the remaining inherent functionality of the heart, create the optimal strain/strain rate profiles for the heart 11.

In FIG. 1, a band line 34 is shown that represents the ventricular epicardium on the heart 11. To understand strain ε(t) in the heart 11, it should be imagined that the band line 34 is opened and flattened into a straight line. The band line 34 has a length L1. When the heart 11 contracts, that band line 34 has a shorter length L2. In the heart 11, strain ε(t) is the change in length ΔL over the initial length L1. Since the heart 11 can be considered as containing many stacked layers, both above and below the ventricular epicardium, strain ε(t) varies along the length and is therefore a function of length.

Figure 3:
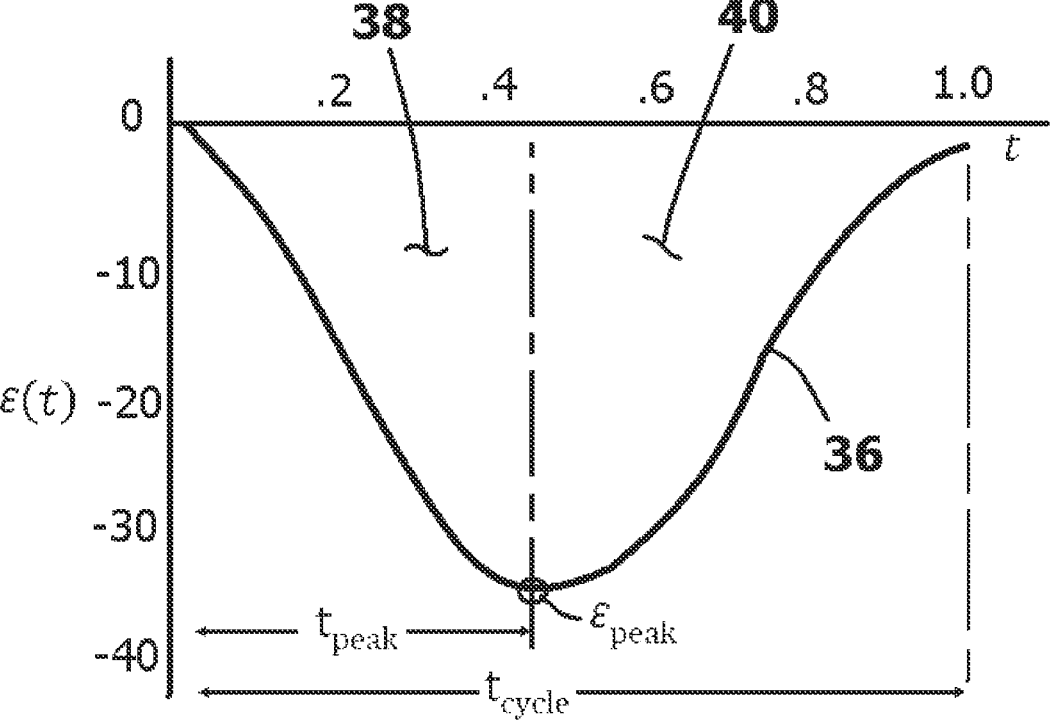
FIG. 3 is a graph showing an exemplary ventricular strain profile produced by the cardiac support device of the present invention system.

The cardiac support device 20 is controlled by drive profiles 30 in a manner that alters the ventricular strain profiles of the heart 11 in a complementary manner. Referring to FIG. 3, an optimal ventricular strain profile 36 for a healthy heart is shown, wherein the heart is average for the physiology of the patient. Such an optimal ventricular strain profile 36 can be generated for any heart of a given AV diameter $D_{(ED)}$. As can be seen, the strain ε(t) has a compression phase 38 and a retraction phase 40 over time (t). As can also be seen, there is a peak strain $\varepsilon_{(peak)}$, a time to peak strain t(peak), and an overall cycle period t(cycle).

An estimation for the strain ε(t) in the compression phase 38 can be estimated using the following equation:

$$\varepsilon(t) = \frac{\varepsilon_{peak}}{2}\left(\sin\left(\frac{\pi}{t_{peak}} \times t - \frac{3}{2}\pi\right) - 1\right) \qquad \text{Equation 1}$$

An estimation for the strain ε(t) in the retraction phase 40 can be estimated using the following equation:

$$\epsilon(t) = \frac{\epsilon_{peak}}{2}\left(\sin\left(\frac{\pi}{t_{cycle} - t_{peak}} \times (t - t_{peak}) - \frac{\pi}{2}\right) - 1\right) \qquad \text{Equation 2}$$

The value for $\varepsilon_{(peak)}$ can be estimated from the measured AV diameter $D_{(ED)}$ of the heart 11 using the following equation:

$$\varepsilon_{(peak)} \approx -0.1254(D_{(ED)}) - 7.7135 \qquad \text{Equation 3}$$

The value for $t_{(cycle)}$ is determined by the following equation.

$$t_{(cycle)} = (\text{Activation Rate}/60)^{-1} \qquad \text{Equation 4}$$

The activation rate can be determined from the measured diameter $D_{(ED)}$ using the following equation.

$$\text{Activation Rate} \approx -1.2089 \, D_{(ED)} + 221.46 \qquad \text{Equation 5}$$

From the above description and equations, it will be understood that an optimal ventricular strain profile 36 for healthy hearts of different physiologies can be estimated. What remains is the problem of how to actively control the cardiac control device 20 so that it applies the needed strains to a damaged or diseased heart so that the heart can better function near its optimal strain profile.

Figure 4:
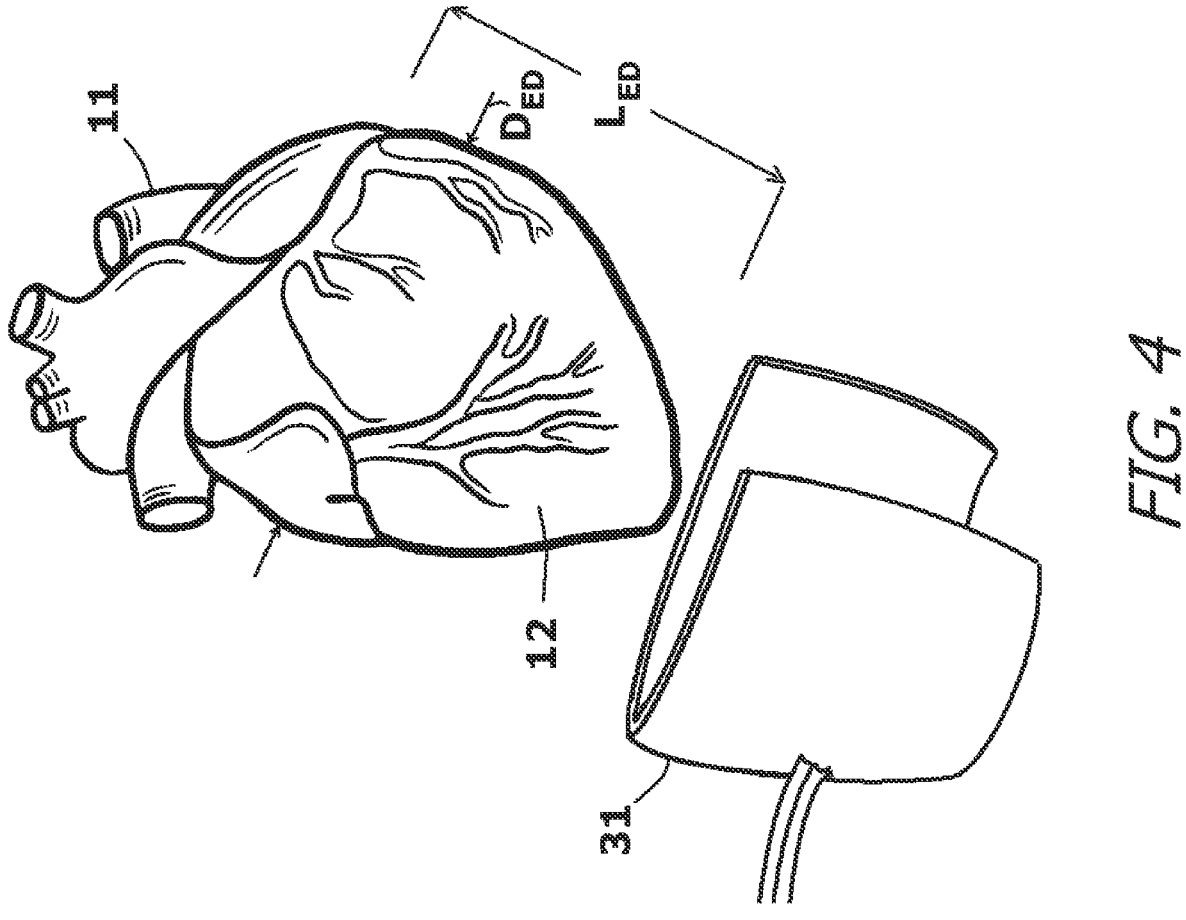
FIG. 4 shows an alternate embodiment for the cardiac support device, that has a different area of contact than that of the exemplary embodiment of FIG. 1 and FIG. 2.

In FIG. 2, the cardiac control device 20 has a band that encircles the heart. Referring to FIG. 4, an alternate embodiment is shown, wherein the cardiac support device 31 does not encircle the heart 11 but contacts areas of the heart 11. Depending upon the size of the heart 11 and the make and model of the cardiac support device, there will be different areas of contact onto which forces are applied to the heart 11.

Figure 5:
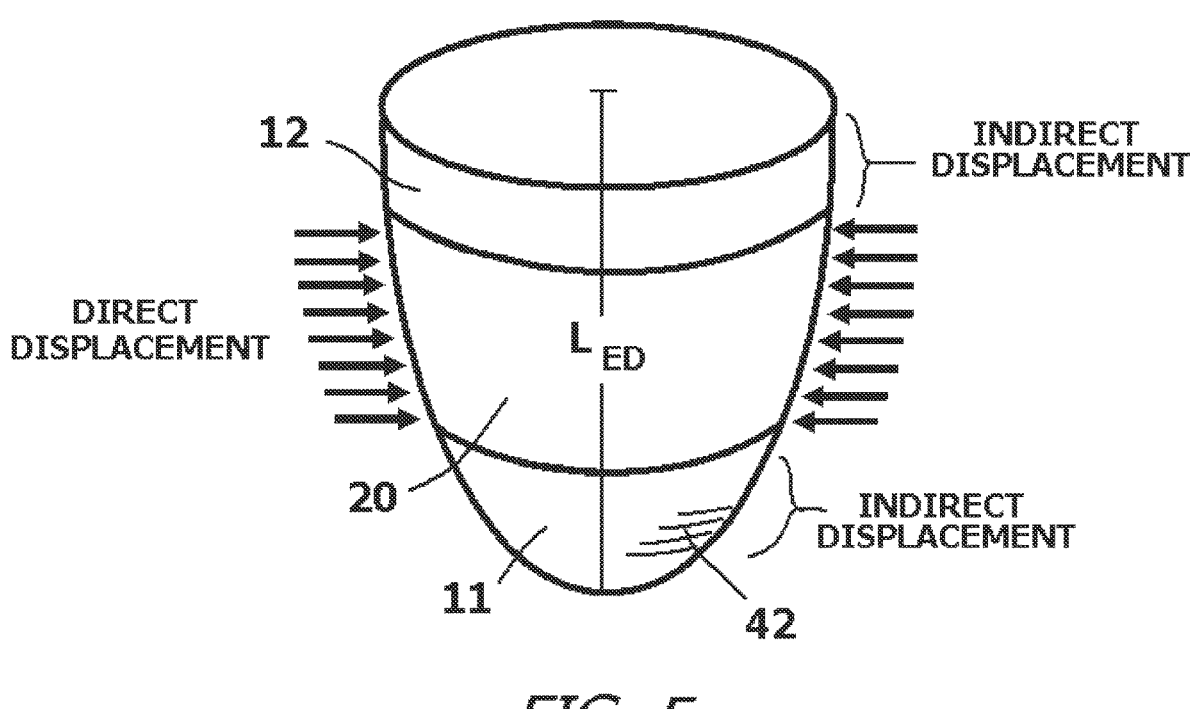
FIG. 5 shows the cardiac support device in engagement with a heart to illustrate surface area of contact and areas of displacement.

Referring to FIG. 5 in conjunction with FIG. 2, it will be understood that the exemplary cardiac support device 20 is applied to the heart 11 so that the cardiac support device 20 covers all, or part, of the ventricles 12. Accordingly, the surface area on the heart 11 that the cardiac support device 20 engages is very important in determining how much strain the cardiac support device 20 must supply. The force that the cardiac support device 20 applies to the heart 11 is divided by the surface area of contact. As such, a cardiac support device 20 that covers only part of the ventricles 12 must apply more force than one that covers most all of the ventricles 12, since force is inversely proportional to surface area.

Furthermore, if the cardiac support device 20 covers only part of the heart 11, as is shown, the cardiac support device 20 creates both direct displacement and indirect displacement of the heart tissue. Direct displacement is created by the forces applied directly to the heart 11 by the cardiac support device 20. These direct forces compress the heart 11. This direct compression, in turn, causes displacement in adjacent heart tissue that is not in contact with the cardiac support device 20. This indirect displacement also alters the shape and volume of the heart 11. These changes can cause a change in beat rhythm. To further complicate matters, the direct displacement and the indirect displacement created by the cardiac support device 20 combine to elongate the heart 11. That is, the displacements provided by the cardiac support device 20 make the measured length $L_{(ED)}$ longer. As the heart elongates, a smaller percentage of the heart 11 remain in direct contact with the cardiac support device 20. This reduces contact surface area. This, in turn, requires that the contact surface area supply greater forces to maintain the same compression forces on the heart 11. The changes in the pressures that the cardiac support device 20 must provide as a function of surface area are shown in the graph of FIG. 6.

Figure 6:
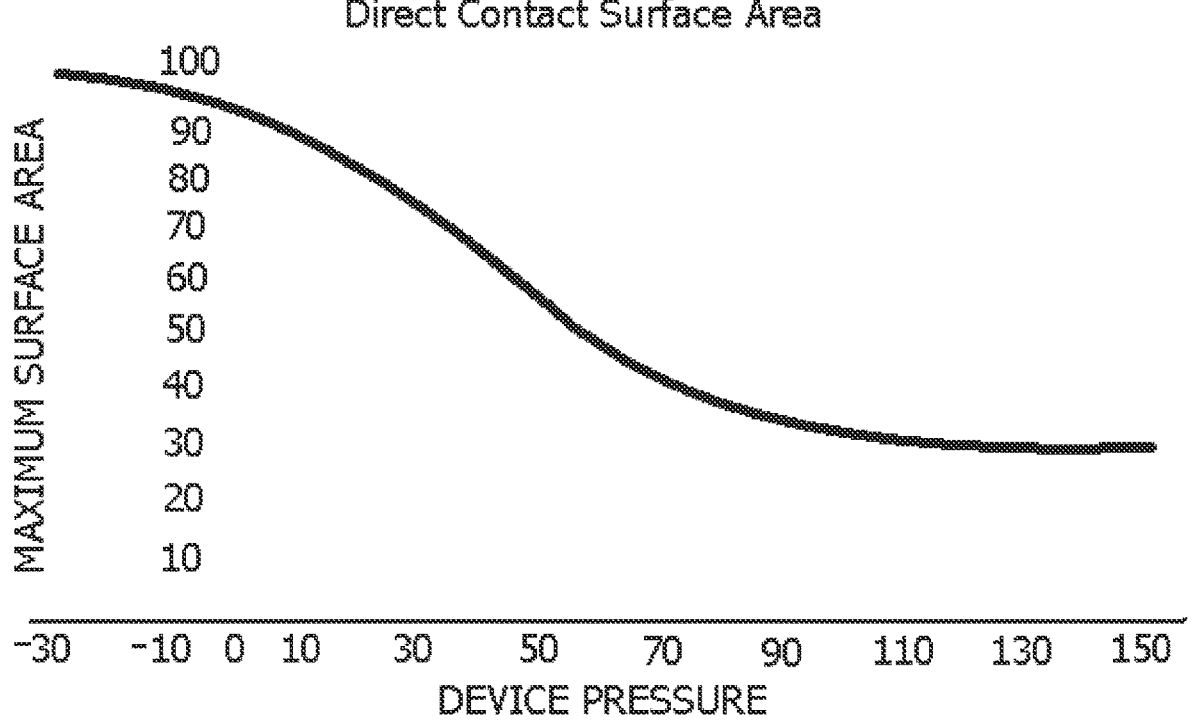
FIG. 6 is a graph that plots surface area of contact with pressures needed to be generated by the cardiac support device.

Referring to FIG. 5 in conjunction with FIG. 6, it will be understood that as the heart 11 elongates, changes in the volume of the heart 11 can be estimated by imagining the heart as a series of stacked disks 42 that number 1 to (n). Some of those stacked disks 42 are in the area of direct displacement. Other of the stacked disks 42 are in the areas of indirect displacement. The volume of each disk 42 in the area of direct displacement can be estimated using the following equation.

$$V_{Disk} = \pi\left(r_0\left(1 + \frac{\text{Strain}}{100}\right)\right)^2 h \qquad \text{Equation 6}$$

The variable "$V_{disk}$" is the volume of the disk. The variable "$R_o$" is the original radius of the disk. The variable "H" is the height selected for the disk, which is the length increment between disks. The variable "n" is the number of disks.

The volume of the disks in the areas of indirect displacement can be estimated using the following equation.

$$V_{Disk} = \pi (r_0)^2 h \qquad \text{Equation 7}$$

The total volume of displacement can therefore be estimated using the following equation.

$$V_{total} = \sum_{i=1}^{n} V_{Disk_n} \qquad \text{Equation 8}$$

Accordingly, the changes in volume of the heart 11 created by the application of compression forces by the cardiac support device 20 can be estimated. Changes in volume correspond to changes in heart length, which correspond to changes in surface area and pressure requirements via the graph of FIG. 6.

Returning to FIG. 1 and FIG. 2, it will be understood that the central processing unit 28 has various inputs. If stain gauges 32 are used to measure ventricular strain, then the central processing unit 28 is connected to the strain gauges 32 imbedded into the cardiac support device 20. In this manner, the central processing unit 28 can directly monitor strains and strain profiles in real time. If ventricular strain is measured using strain scan data from a heart imaging machine, then that strain scan data is fed to the central processing unit 28. Furthermore, the central processing unit 28 can receives signals from one or more other pieces of heart monitoring equipment 16. Such heart monitoring equipment 16 can monitor heartrate by blood flow rate, arterial pressure, electrocardiogram, peak strain, or the like. In this manner, the central processing unit 28 can dynamically monitor heart rate.

A user interface 44 is provided, wherein medical personnel can enter the type of cardiac support device 20 being used and the heart physiology of the patient. Given heart physiology and the make and model of the cardiac support device 20, the contact area between the heart 11 and the cardiac support device 20 of the heart 11 can be readily determined. The contact area corresponds to the area of direct displacement that will be affected by the cardiac support device 20. Given heart physiology and contact area, the area of indirect displacement can also be determined.

The central processing unit 28 runs application software 25 that synchronizes the operation of the cardia support device 20 with the heart in two ways. In a first process, a rhythm synchronization is achieved where the contraction of the cardiac support device 20 correspond to the rhythm of the heart. In a second process, the forces applied by the cardiac support device are dynamically adjusted to achieve proper mechanical cardiac synchrony. That is, the applied forces improve ventricular function by encouraging the ventricular muscles to contract in a more synchronous manner and alter the cardiac contractions from a dyssynchronous pattern to a more favorably pattern.

Figure 7:
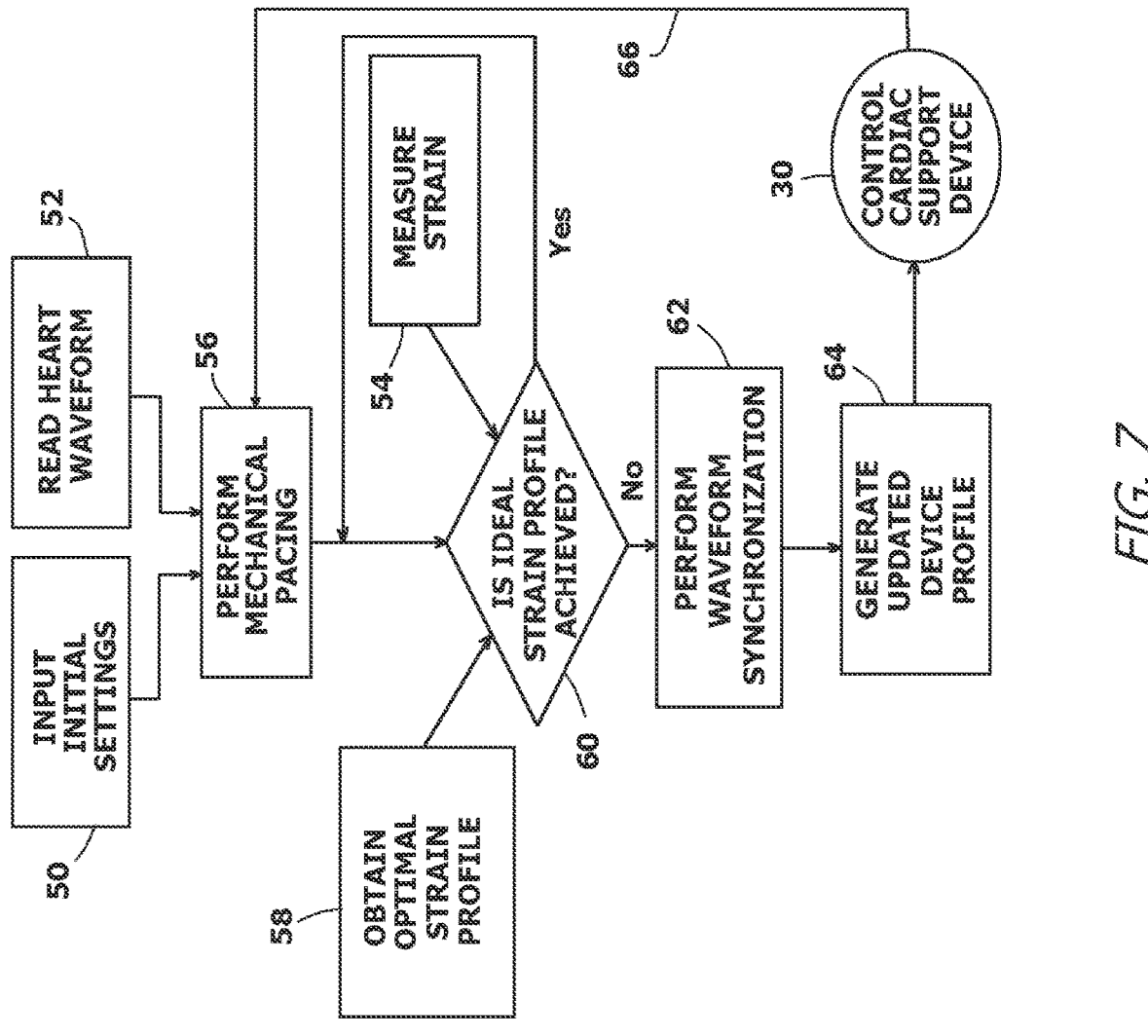
FIG. 7 is a flow diagram that illustrates an exemplary operating methodology.

Referring to FIG. 7 in conjunction with FIG. 1 and FIG. 2, it will be understood that initial settings, such as the make/model of the cardiac support device 20 and the physiology of the heart 11 are entered. See Block 50. Likewise, the central processing unit 28 reads the dynamic variables. The dynamic variables include the strain readings from the strain gauges 32, or strain scans, and the heart waveform from the heart monitoring equipment 16. See Block 52 and Block 54.

The first process is rhythm synchronization where the contraction rate utilized by the cardiac support device 20 is matched to the contraction rate of the heart 11. As indicated by Block 56, rhythm synchronization is premised on the understanding that over time, the heart's inherent contraction rate may vary and therefore, re-interrogation is performed periodically to ensure the heart 11 and the cardiac support device 20 are at optimal synchronization. That is, the heart rate is continuously or periodically sampled using the readings from the heart monitoring equipment 16. The detected heart rate is then used to pace the cardiac support device 20. In this manner, the cardiac support device 20 can improve the heart's pump function while reducing the chance of the heart 11 working independently, which may put undue pressure on the heart 11 that is not fully functional.

The inherent beat rate of the heart 11 varies, but can be averaged over a period of time. The heart monitoring equipment 16 monitor heartrate by blood flow rate, arterial pressure, electrocardiograms, peak strain, or the like. In this manner, the central processing unit 28 can dynamically monitor heart rate. The central processing unit 28 generates drive profiles that begins the contraction of the cardiac support device 20 at the same moment that the heart 11 begins ventricular contraction.

Once the rhythm synchronization is optimized, the second process of achieving mechanical cardiac synchrony is started. The strain readings from the heart 11 are considered and are used to generate the drive profiles 30 that control the cardiac support device 20. One or more physiological parameters for the heart 11, such as size, is input into the central processing unit 28. Accordingly, an optimal strain profile 58 for a heathy heart having such parameters can be mathematically calculated. The central processing unit 28 attempts to achieve mechanical cardiac synchrony. Mechanical cardiac synchrony corresponds to the complex ventricular contractions that occur in the heart 11. The manner in which the ventricles contract can be quantified using strain analysis. Strain analysis can look at all different areas of the heart 11 and determine if contractions follows a relatively ideal contraction "profile". Mechanical cardia synchrony for the heart 11 is achieved when the ventricular strain profile measured for the heart 11 matches the optimal strain profile 58. To do this, the central processing unit 28 generates drive profiles 30 for the cardiac support device 20 so that the forces applied by the cardiac support device 20 combine with the inherent functionality of the heart 11 to create a modified strain profile that approaches that of the optimal strain profile 58.

The goals of mechanical cardiac synchrony are three-fold. The first goal is to improve the heart's native contractile function, although it may have been severely or partially compromised. The second goal is to improve the likelihood that the compression cycle of the cardiac support device 20 is synchronized with that of the compression cycle for the heart 11. Lastly, the third goal is to improve the likelihood that that mechanical stimulus of the cardiac support device 20 leads to the mechanical contraction of the heart 11. When the heart 11 has no intrinsic pulses, the cardiac support device 20 can, therefore, stimulate the synchronization, and then adjust the level of external support based on how much the heart's native functions are restored.

When heart function is measurable, e.g., greater than approximately 20% of normal function, it is possible to accurately synchronize the cardiac support device 20 with the heart's native or intrinsic cyclic pump function. As is indicated by Block 60, after mechanical pacing is complete, the central processing unit 28 compares the strain profile measured directly from the strain gauges 32 to the optimal strain profile 58. If the measured strain profile is not the same as the optimal strain profile 58, then corrective measures are taken. The drive profiles 30 generated by the central processing unit 28 control the physical operation of the cardiac support device 20.

Accordingly, different drive profiles 30 cause the cardiac support device 20 to produce different pressure waveforms. The pressure waveforms are estimations produced using the formulations for strain previously described. The differences in strain profiles between the measured strain profiles and the optimal strain profile 58 are known. A drive profile 30 is generated that creates a strain profile that, when added to the measured strain profile, should approach the value of the optimal strain profile. The strain profile generated by the cardiac support device 20 in response to a drive profile 30 is compared to the heartbeat waveform detected by the heart monitoring equipment 16. See Block 62. Upon comparison of the waveforms, a coordination index (CI) between the two waveforms can be calculated using the following equation.

$$CI = \sqrt{\frac{1}{N-1}\sum_{i=1}^{N}(d_i - \overline{d})^2} \qquad \text{Equation 9}$$

The variable "$d_i$" is the time delay between peak heart signal (physiologic waveform) and device pressure waveform over one device pressure cycle. The variable "$d$" is the average delay over N number of cycles. The variable "N" is the number of consecutive cycles in recording (e.g., N can be any number greater than 3, but N>10 or any other arbitrary number with increasing N leading is preferred to increase accuracy. The coordination index (CI) is basically the standard deviation of delay between peaks.

During the waveform synchronization procedure, it will be understood that the physiologic waveform and the pressure waveforms of the cardiac support device 20 are compared and the difference in timing of peaks are analyzed. If it is determined that each physiologic peak is matched with a device pressure peak in one cycle, then the match, or lack thereof, is assessed over multiple cycles. If higher variability between peak mismatches are seen over repeated cycles, then an updated device profile 30 is created. See Block 64. The device profile 30 can be updates using any combination of three options. The peak time ($t_{peak}$) of the cardiac support device 20 can be adjusted. Second, the mechanical pacing can be adjusted so that the frequencies of contraction better align. Third, the peak strain ε(peak) produced by the cardiac support device 20 can be adjusted. If one or more of these corrective actions idealizes mechanical synchrony, then the device-specific pressure waveform is achieved. If mechanical cardiac synchrony is not idealized, then the adjustments are repeated. See loop line 66.

Figure 8:
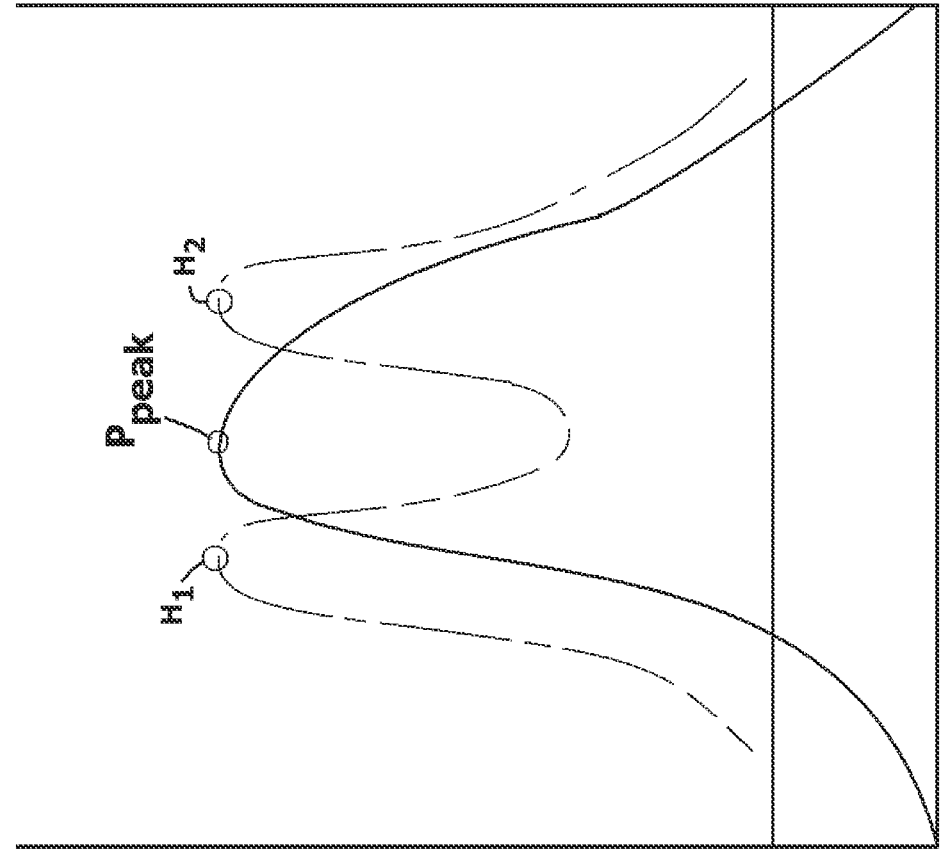
FIG. 8 is a graph depicting the cycles featuring loss of ventricular capture.

Referring to FIG. 8, a graph 70 is shown that illustrates the identification of the cycles featuring loss of ventricular capture. Loss of ventricular capture occurs when number of peaks from the heartbeat waveform is greater than 1. This is $H_1$, $H_2$ and the time between the two adjacent peaks is more than a certain percentage of the length of the device pressure cycle, e.g., >10% of the cycle length with less cycle length indicating more synchrony. It should be understood that the loss of ventricular capture, as represented in FIG. 8, can be detected, and can be corrected in the same manner in the same manner as that set forth in the methodology of FIG. 7. That is, the degree of loss can be detected, and an optimal device profile can be generated to minimize the loss in ventricular capture.

It will be understood that the embodiments of the present invention that are illustrated and described are merely exemplary and that a person skilled in the art can make many variations to those embodiments. All such embodiments are intended to be included within the scope of the present invention as defined by the claims.

What is claimed is:

1. A method of supporting functionality of a patient's heart with a cardiac support device, wherein said patient's heart has a beating rhythm, an inherent pumping functionality, and a physiological strain profile, said method comprising the steps of:

determining an optimal strain profile for the patient's heart;

providing a cardiac support device that contains compartments that expand and contract with changes in pressure;

providing a valve manifold that is connected to an external pressure source, wherein the changes in pressure within said compartments of said cardiac support device are selectively controlled by operation of said valve manifold;

placing said cardiac support device in position to affect said patient's heart, wherein said cardiac support device selectively applies mechanical forces externally to said patient's heart that act to compress said ventricles;

monitoring said patient's heart to determine said beating rhythm and said physiological strain profile;

operating said valve manifold to create a pressure profile in said compartments of said cardiac support device, wherein said cardiac support device applies said mechanical forces to the patient's heart that are a result of said drive pressure profile-received;

controlling said valve manifold so that said cardiac support device applies said mechanical forces externally to said patient's heart in synchronization with said beating rhythm so that said mechanical forces applied by said cardiac support device combine with said inherent pumping functionality of the patient's heart to produce a modified strain profile that is closer to said optimal strain profile than said physiological strain profile.

2. The method according to claim 1, wherein monitoring said patient's heart includes monitoring a biometric variable of said patient's heart, wherein said biometric variable is selected from a group consisting of flow rate, arterial pressure, electrocardiogram, and ventricular strain.

3. The method according to claim 1, wherein determining said optimal strain profile for the patient's heart includes calculating said optimal strain profile for a healthy heart of similar physiological characteristics to said patient's heart.

4. The method according to claim 1, wherein said modified strain profile contains a peak strain, a time to peak strain, and a cycle time.

5. The method according to claim 4, wherein said modified strain profile is compared to said optimal strain profile and said mechanical forces externally applied by said cardiac support device are modified to cause said modified strain profile to be closer to said optimal strain profile.

6. The method according to claim 5, wherein said mechanical forces externally applied by said cardiac support device are selectively changed to alter an element of said modified strain profile, wherein said element is selected from a group consisting of said peak strain, said time to peak strain, and said a cycle time.

7. The method according to claim 4, wherein said modified strain profile is further modified by altering said peak strain.

8. The method according to claim 4, wherein said modified strain profile is further modified by altering said time to peak strain.

9. The method according to claim 4, wherein said modified strain profile is further modified by altering said cycle time.

10. The method according to claim 1, wherein placing said cardiac support device in position produces an area of contact between said cardiac support device and said patient's heart, wherein said mechanical forces produced by said cardiac support device act upon said patient's heart, therein altering said beating rhythm.

11. The method according to claim 1, wherein placing said cardiac support device in position produces an area of contact between said cardiac support device and said patient's heart, wherein mechanical forces produced by said cardiac support device act upon said patient's heart, therein producing an altered area of contact, and therein producing an altered heart size.

12. The method according to claim 11, wherein said altered heart size is used in determining an updated size for said patient's heart and updating said optimal strain profile for a healthy heart of said updated size.

13. The method according to claim 11, wherein said altered area of contact is used in determining said mechanical forces externally applied to said patient's heart by said cardiac support device.

14. The method according to claim 1, wherein placing said cardiac support device in position creates an area of contact between said cardiac support device and said patient's heart, wherein said cardiac support device produces an altered area of contact when activated, and thereby produces an altered heart size and an altered beating rhythm, and wherein said altered heart size is used in determining said optimal strain profile.

15. The method according to claim 14, wherein said altered area of contact and said altered beating rhythm are used in determining said physiological strain pattern to be applied to said patient's heart by said cardiac support device.

* * * * *